Aug. 26, 1958 J. A. KERNODLE Plant Pat. 1,744
PECAN TREE
Filed Dec. 5, 1957
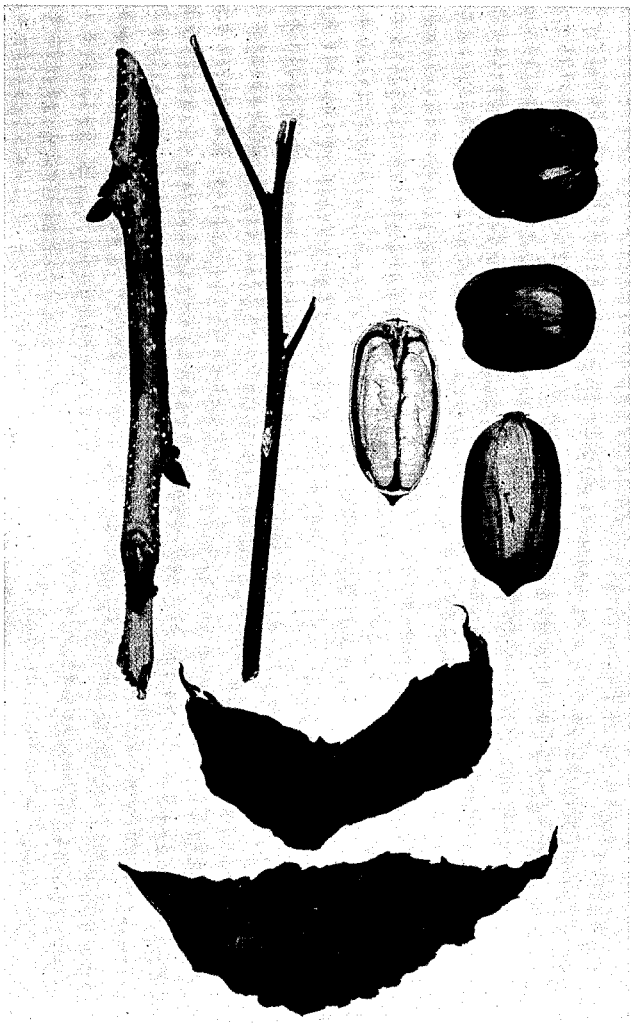
INVENTOR
J. A. Kernodle
BY Cobb & Cobb
ATTORNEYS United States Patent Office Plant Pat. 1,744
Patented Aug. 26, 1958

1,744

PECAN TREE

Julius A. Kernodle, Camp Hill, Ala., assignor to Simpson Nursery Company, Monticello, Fla., a partnership Application December 5, 1957, Serial No. 700,925

1 Claim. (Cl. 47—62)

The present invention relates to a new and distinct variety of pecan tree which apparently originated as a sport of a Frotscher graft (unpatented) grown on cultivated property at Camp Hill, Alabama.

At the time the new variety first came to my attention, I was, and for many years previously had been, engaged in the business of buying crops of pecan nuts in the area of Camp Hill, Alabama, during the course of which I came across an unusual and exceptionally fine nut borne by a tree growing out of an old root or stump of a small pecan tree, believed to have been a Frotscher graft, which had been planted in a lot where it ultimately was broken off down to the ground level as the result of the pasturing of livestock on said lot. After carefully studying the nuts of the new tree which grew out of the old root or stump aforesaid, I recognized from my long and wide knowledge of pecan varieties that they were unlike those of any known variety, and I therefore obtained permission from the owner of the new tree to take budwood therefrom which I personally budded on my own property at Camp Hill, Alabama. Continued observation of my budded trees confirmed the unusual and fine qualities which I initially observed in the nuts of the parent tree, as well as establish other outstanding and distinctive characteristics which may be briefly summarized as follows, and which represent a unique and desirable combination never before known, so far as I am aware:

(1) Luxuriant foliage, with leaves being larger in size than those of many other varieties;

(2) Large size and blunt shape of the nuts;

(3) Extremely thin nut shells, which tend to readily crack down the middle when subjected to hand pressure, and the nuts being lighter in color than those of the "Stuart" variety (unpatented) and having an almost polished appearance;

(4) Nut meats or kernels of a color much lighter than those of most other pecan varieties, said kernels being full and oily, but never dry or shucky, and being of excellent quality and flavor, the flavor resembling somewhat that of walnuts, but being still predominantly a pecan flavor; and (5) A nut-ripening habit which is later than that of many other varieties.

The accompanying drawing shows typical specimens of the foliage, wood and nuts of this new pecan variety as depicted in color as nearly true as it is reasonably possible to make the same in a color illustration of this character, with both the upper and under surfaces of the leaves being shown as well as both mature and immature wood, and one of the nut specimens being shown in longitudinal cross-section to illustrate its thin shell, while exposing the meat or kernel in elevation.

The following is a detailed description of the new variety aforesaid, with color terms in accordance with Koster's Color Guide, except where general color terms of ordinary dictionary significance are obvious, as based upon observations made at Camp Hill, Alabama and at Monticello, Florida:

Parentage: Uncertain, but believed to be a sport of Frotscher graft.

Tree: Large-sized; good productivity; vigorous and hardy growth habit; medium-sized limbs.

*Old wood.*—Smooth. Color—between Ashy Grey, Plate 99, and Pearl Grey, Plate 100.

*New wood.*—Color—near Moss Green, Plate 76.

Foliage:

*Size.*—From medium to large.

*Quantity.*—Abundant.

*Color.*—Upper surface—near Boxwood Green, Plate 79. Under surface—near Lettuce Green, Plate 74.

Buds: Medium size. Color—near Van Dyck Brown, Plate 96.

Nuts:

*Ripening habit.*—Even.

*Time of harvesting.*—From about October 21 to about November 10.

*Quantity.*—Abundant.

*Maturity.*—Medium late (usually between first week in September to last week in October).

*Tenacity.*—Free.

*Cluster.*—Large size. Average number of nuts to cluster—usually from 3 to 5.

*Individual nuts.*—Length—from about 1½ inches to 2 inches. Diameter—about ¾ inch. Average number to pound—from 55 to 70. Shape—long, with blunt base and only slightly tapered point. Shell—very thin; cracks and releases very easily; color—between Fawn, Plate 89, and Bistre, Plate 93, with longitudinal stripes or streaks of Sepia, Plate 87, toward apex. Kernel: Color—near Buff, Plate 80; flavor—excellent; shape—tapers only very slightly toward tip; texture—very firm; sutures—even.

Disease resistance: Good resistance to scab, as determined by comparison with other varieties grown in the nursery row under comparable cultural conditions at Monticello, Florida.

I claim:

A new and distinct variety of pecan tree, substantially as herein shown and described, characterized particularly as to novelty by its luxuriant and relatively large foliage, the large size and blunt shape of its nuts and their extremely thin shells which tend to readily crack down the middle when subjected to hand pressure, the relatively light color and almost polished appearance of its nuts, the full and oily kernels and their relatively light color, excellent quality and flavor, and its relatively late nut-ripening habit.

References Cited in the file of this patent

Publication: Proceedings of the 36th and 37th meetings of the American Pomological Society for 1919 and 1920, page 178.